United States Patent [19]

Robins et al.

[11] Patent Number: 4,950,647
[45] Date of Patent: Aug. 21, 1990

[54] T CELL IMMUNOPOTENTIATOR

[75] Inventors: Roland K. Robins; Brahma S. Sharma; Ganapathi R. Revankar, all of Irvine, Calif.

[73] Assignee: Nucleic Acid Research Institute, Costa Mesa, Calif.

[21] Appl. No.: 253,050

[22] Filed: Oct. 4, 1988

[51] Int. Cl.$^5$ ............... A61K 31/395; A61K 31/70; C07H 19/123
[52] U.S. Cl. ................... 514/45; 514/885; 536/23; 536/24; 424/85.1; 424/85.2
[58] Field of Search ............ 536/23, 24; 514/45, 514/885

[56] References Cited

U.S. PATENT DOCUMENTS

3,919,193 11/1975 Mian et al., ............ 200/211.5 R
4,056,674 11/1977 Robins et al. ............ 536/28
4,780,313 10/1988 Koichiro et al. ............ 424/88

OTHER PUBLICATIONS

Ganapathi R. Revankar et al., *J. Medicinal Chemistry*, vol. 27, 1389, (1984).

Primary Examiner—John W. Rollins
Assistant Examiner—Gary L. Kunz
Attorney, Agent, or Firm—Herb Boswell

[57] ABSTRACT

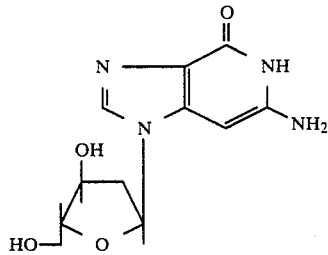

6-Amino-1-(2-deoxy-αD-erythro-pentofuranosyl-)imidazo [4,5-C]pyridin-4-one (also know as α-2'-deoxy-3-deazaguanosine) is non mitogenic to human peripheral blood lymphocytes; however, it displays a potent immunoenhancing activity on human T cells. This compound causes a marked increase in both phytohemagglutinin and Concanavalin A induced proliferation of T cells. When added during allogeneic mixed lymphocyte response, it also potentiates the proliferation of alloreative T cells. The compound shows no potentiating effect on B lymphocytes activated either with *Staphylococcus aureus* cowan or Pokeweed mitogen, suggesting that it is mainly a T cell function immunopotentiator. The compound overcomes induced immunosuppression and is able to restore depressed proliferative responses of T cells. Further it potentiates the generation of antigen-specific primary cytotoxic T lymphocytes.

10 Claims, 2 Drawing Sheets

FIG. 1

-●-, NO PHA; -◆-, 0.13 μg/0.2 ML; -□-, 0.25 μg;
-■-, 1 μg; AND -▲-, 4 μg PHA.

FIG. 2

-●-, NO CONCANAVALIN A; -⊙-, 0.13 μg/0.2 ML;
-⊡-, 0.25 μg; AND -■-, 1 μg.

T CELL IMMUNOPOTENTIATOR

BACKGROUND OF INVENTION

This invention is directed to the use of the compound 6-amino-1-(2-deoxy-α-D-erythro-pentofuranosyl-)imidazo[4,5-C]-pyridin-4-one as an immunoenhancing agent, an immunoadjuvant agent, an immunopotentiating agent and as a immunorestorative agent especially for human T cells.

Certain C8 substituted guanosine derivatives have been reported to display immunostimulatory activity. These derivatives, 8-bromoguanosine, 8-mercaptoguanosine and 7-methyl-8-oxoguanosine, have demonstrated the ability to stimulate proliferation of B cells, see Goodman, M. G. and W. O. Weigle, "Activation of lymphocytes by a thiol-derivatized nucleoside: characterization of cellular parameters and responsive subpopulations", *J. Immunol.*, 130:551, 1983; Goodman, M. G. and W. O. Weigle, "Intracellular lymphocytes activation and carrier-mediated transport of C8-substituted ribonucleosides", *Proc. Natl. Acad. Sci. USA*, 81:862, 1984; and Goodman, M. G. and W. O. Weigle, "Induction of immunoglobulin secretion by a simple nucleoside derivative", *J. Immunol.*, 128:2399, 1982. This effect is exerted predominantly upon a subset of mature B lymphocytes and to a lesser degree on a subset of immature B cell.

In addition these C8 substituted guanosine nucleosides have also been shown to be capable of (a) augmenting polyclonal activation of B cells to secrete immunoglobulins in both murine and human systems, (b) increasing thymus dependent and thymus independent antibody immune responses and (c) transmitting T cell like inductive signals to B cells, see Goodman, M. G. and W. O. Weigle, "T cell-replacing activity of C8-derivatized guanine ribonucleosides", *J. Immunol.*, 130:2042, 1983; Goodman, M. G. and W. O. Weigle, "Manifold amplification of in vitro immunity in normal and immunodeficient mice by ribonucleosides derivatized at C8 of guanine", *Proc. Natl. Acad. Sci. USA*, 80:3452, 1983; and Goodman, M. G. and W. O. Weigle, "Derivatized guanosine nucleosides: a new class of adjuvant for in vitro antibody responses", *J. Immunol.*, 130:2580, 1983. Recently, 8-bromoguanosine was also shown to activate macrophages and NK cells. This group of compounds is further described in U.S. Pat. Nos. 4,539,205, 4,643,992 and 4,746,651.

Another group of low molecular weight compounds, certain pyrimidinones, have also been reported to increase the level of polyclonal and antigen-specific antibody production, see Skulnick, H. I., S. D. Weed, E. E. Edison, H. E. Renis, W. Wierenga, and D. A. Stringfellow, "Prymidinones 12-Amino-5-halo-6-aryl-4(3H)-pyrimidinones interferon-inducing antiviral agent", *J. Med. Chem.*, 28:1864, 1984; Fast, P.E. D. A. Hattfield, and D. A. Stringfellow, "Polyclonal B cell activation and stimulation of specific antibody responses by 5-Halo-pyrimidones with antiviral and antineoplastic activity", *J. Biol. Reso. Modif.*, 1:199, 1982; and Lotzova, E., C. A. Savary, and D. A. Stringfellow, "5-Halo-6-phenylpyrimidinones: new molecules with cancer therapeutic potential and interferon inducing capacity are strong inducer of murine natural killer cells", *J. Immunol.*, 139:965, 1983. In addition, these pyrimidinones were found to enhance interferon release and NK cell activity and induced cytotoxic macrophages. Both of these C8 substituted guanosines and pyrimidinones however were unable to activate T cells.

T lymphocytes are involved in the generation of effector cytotoxic antibody, and cytotoxic and immunoregulatory T cells. They mediate regulation of cellular and humoral responses by interacting target populations either via direct cell to cell contact or by secretion of a cascade of lymphokines and suppressor factors that provide proliferative, differentiation and immunosuppressive signals.

Cytotoxic T lymphocytes have been shown to play an important role in defense against viruses and neoplasms. Adoptive transfer of H-2 restricted cytotoxic T lymphocytes with high degree specificity was recently shown to protect T cell deficient mice with influenza pneumonia. Similarly, mice, or rats with established tumors were cured or their lives were prolonged following transfer of specific cytotoxic T lymphocytes expanded in vitro with interleukin-2. It has also been reported (see Sharma, B. and S. Gupta, "Antigen-specific primary cytotoxic T lymphocyte response in acquired immune deficiency syndrome (AIDS) and AIDS related complex", *Clin. Exp. Immunol.*, 62: 296, 1985) that interleukin-2 could restore depressed cytotoxic T cell function in some AIDS patients and patients with AIDS related complex.

Intrinsic or acquired abnormality in any of these T cells or their functions can lead to the development of cancer, viral and other infections, immunodeficiency disorders and autoimmune diseases.

The synthesis and limited in vitro antiviral activity of the compound 6-amino-(2-deoxy-α-D-erythro-pentofuranosyl)imidazo[4,5,-C]pyridin-4-one is reported in Revankar, G. R., P. K. Gupta, A. D. Adams, N. K. Dalley, P. A. McKernan, P. D. Cook, P. G. Canonico, and R. K. Robins, "Synthesis and Antiviral/antitumor activities of certain 3-Deazaguanine nucleosides and nucleotides", *J. Med. Chem.*, 27:1389, 1984. Further in this report the compound 6-amino-(2-deoxy-α-D-erythro-pentofuranosyl)-imidazo[4,5,-C]pyridin-4-one is noted as being devoid of any useful antitumor activity.

BRIEF DESCRIPTION OF THE INVENTION

It has been found that the compound 6-amino-(2-deoxy-α-D-erythro-pentofuranosyl)-imidazo[4,5,-C]pyridin-4-one is a potent immunoenhancing agent of human and animal cells. It can potentiate both T cell mitogen and alloantigen-induced proliferation of human lymphocytes and is useful as an immunoadjuvant. Additionally it can potentiate the generation of antigen specific cytotoxic T lymphocytes. Further it reverses suppression of T cell responses including artificially induced suppression of T cell response and is useful to reverse suppression of T cell responses as, for instance, those caused by immunosuppressive or chemotherapeutic agents.

The present invention thus relates to the use of the compound 6-amino-(2-deoxy-α-D-erythro-pentofuranosyl)imidazo[4,5,-C]pyridin-4-one as an immunostimulator and/or immunopotentiator especially for human and animal T cells.

According to this invention the immunoenhancing properties of the compound 6-amino-(2-deoxy-α-D-erythro-pentofuranosyl)-imidazo[4,5,-C]pyridin-4-one are achieved by administering a composition comprising an immune activator (an antigen) and a diluent amount of a physiologically tolerable carrier admixed with an immunoenhancing effective amount of the compound 6-amino-(2-deoxy-α-D-erythro-pentofuranosyl)-imidazo[4,5,-C]pyridin-4-one or pharmaceutically acceptable salts thereof.

According to this invention the immunoadjuvant effects of the compound 6-amino-(2-deoxy-α-D-erythro-pentofuranosyl)imidazo[4,5,-C]pyridin-4-one are achieved by administering to human or animal cells a composition comprising a T cell mitogenic agent and a diluent amount of a physiologically tolerable carrier admixed with an immunoadjuvant effective amount of the compound 6-amino-(2-deoxy-α-D-erythro-pentofuranosyl)-imidazo[4,5,-C]pyridin-4-one or pharmaceutically acceptable salts thereof.

According to this invention the proliferation of alloreactive T cells by the compound 6-amino-(2-deoxy-α-D-erythro-pentofuranosyl)-imidazo[4,5,-C]pyridin-4-one is achieved by administering to human or animal cells a composition comprising an alloantigen and a diluent amount of a physiologically tolerable carrier admixed with a proliferative effective amount of the compound 6-amino-(2-deoxy-α-D-erythro-pentofuranosyl)-imidazo[4,5,-C]pyridin-4-one or pharmaceutically acceptable salts thereof.

According to this invention the potentiation of cytotoxic T lymphocytes by the compound 6-amino-(2-deoxy-α-D-erythro-pentofuranosyl)-imidazo[4,5,-C]pyridin-4-one is achieved by administering to human or animal cells a composition comprising a specific antigen and a diluent amount of a physiologically tolerable carrier admixed with a potentiator effective amount of the compound 6-amino-(2-deoxy-α-D-erythro-pentofuranosyl)-imidazo[4,5,-C]pyridin-4-one or pharmaceutically acceptable salts thereof.

According to this invention the restorative effects of the compound 6-amino-(2-deoxy-α-D-erythro-pentofuranosyl)imidazo[4,5,-C]pyridin-4-one on depressed cytotoxic T cell function are achieved by administering to human or animal cells a composition comprising an immunosuppressor and a diluent amount of a physiologically tolerable carrier admixed with an restorative effective amount of the compound 6-amino-(2-deoxy-α-D-erythro-pentofuranosyl)-imidazo[4,5,-C]pyridin-4-one or pharmaceutically acceptable salts thereof.

This invention also contemplates a method of enhancing an immune response comprising contacting T lymphocytes with an immunoenhancing composition including as its active ingredient an amount of the compound 6-amino-(2-deoxy-α-D-erythro-pentofuranosyl)-imidazo[4,5,-C]pyridin-4-one effective to enhance an immune response.

This invention further contemplates a method of enhancing an immune response comprising contacting T lymphocytes with a T cell mitogen and a composition including as an active immunoadjuvant ingredient an amount of the compound 6-amino-(2-deoxy-α-D-erythro-pentofuranosyl)-imidazo[4,5,-C]pyridin-4-one effective to augment the mitogenic immune response.

This invention additionally contemplates a method of enhancing an alloreactive T cell response comprising contacting T lymphocytes with an alloantigen and a composition including as an active proliferative ingredient an amount of the compound 6-amino-(2-deoxy-α-D-erythro-pentofuranosyl)imidazo[4,5,-C]pyridin-4-one effective to induced an allogeneic proliferative response.

This invention additionally contemplates a method of potentiating antigen specific cytotoxic T lymphocytes comprising contacting T lymphocytes in the presence of a specific antigen with an composition including as an active antigen specific T lymphocyte potentiating ingredient an amount of the compound 6-amino-(2-deoxy-α-D-erythro-pentofuranosyl)-imidazo[4,5,-C]pyridin-4-one effective to potentiate the generation of antigen specific cytotoxic T lymphocytes.

This invention moreover contemplates a method of the restoration of depressed cytotoxic T cell function comprising contacting T lymphocytes with an immunoenhancing composition including as its active ingredient an amount of the compound 6-amino-(2-deoxy-α-D-erythro-pentofuranosyl)-imidazo[4,5,-C]pyridin-4-one effective to stimulate a restorative response of T cell function.

The compositions and methods of the invention may be used on cells in vitro as well as in vivo. For in vivo use, the compositions of the invention can be administered by topical administration, suppository administration or by suitable injection as a solution or suspension subcutaneously, intraperitoneally, intravenously, intramuscularly, intracerebrally or intraorally as in pill or capsule form, or in liquid form as a slurry, suspension or solution. For in vitro use, the compositions of the inventions can be administered by contacting, admixing, expanding, bathing, washing, slurrying, suspending or injecting cells with compositions of the invention as a solid or a liquid form in a slurry, suspension or solution.

The restoration of depressed cytotoxic T cell function can be used to reverse immunosuppressive side effects of certain agents and drugs as, for instances, chemotherapeutic agents or other agents which exhibit immunosuppression as an unwanted side effect.

DESCRIPTION OF THE DRAWINGS

This invention will be better understood when taken in conjunction with the drawings wherein.

DETAILED DESCRIPTION OF THE INVENTION

The present invention contemplates the stimulation, enhancement, potentiation, generation or reconstitution of various immune functions by the compound 6-amino-(2-deoxy-α-D-erythro-pentofuranosyl)-imidazo[4,5,-C]pyridin-4-one to stimulate and enhance immunofunction or correct immuno-incompetent states.

8-Bromoguanosine, 8-mercaptoguanosine and 7-methyl-8-oxoguanosine are know to activate lymphocytes to proliferate. Unlike 8-bromoguanosine, 8-mercaptoguanosine and 7-methyl-8-oxoguanosine, the compound 6-amino-(2-deoxy-α-D-erythro-pentofuranosyl)-imidazo[4,5,-C]pyridin-4-one is unable to directly stimulate lymphocytes to proliferate, i.e. by itself it is not mitogenic. It has been found however that like interleukin-2, it is capable of increasing human lymphocyte response to T cell inducers such as mitogens and alloantigens as, for instance, the mitogens phytohemagglutinin and Concanavalin A. Further it has been found that also like interleukin-2 it potentiates the generation of antigen specific T lymphocytes. Additionally it has been found that it serves to stimulate restoration of depressed cytotoxic T cell function.

These findings are quite unexpected and surprising especially since the β nucleoside analog (i.e. 2′-deoxy-3-deazaguanosine) of this compound is immunosuppressive at the same concentrates that this compound is immunostimulatory and other compounds such as 2′-deoxyguanosine and 3-deazaguanosine are not immune system enhancers.

These findings further suggest that 6-amino-(2-deoxy-α-D-erythro-pentofuranosyl)-imidazo[4,5,-C]pyridin-4-one does not have to first induce cell proliferation in order to display its immunostimulatory potential. The potentiation of T cell response to mitogens by this compound is dose and mitogen dependent. It increases responses to optimal as well as to suboptimal concentrations of mitogens. Although 6-amino-(2-deoxy-α-D-erythro-pentofuranosyl)-imidazo[4,5,-C]pyridin-4-one exhibits enhancing effect at a wide range of concentrations as, for instance from about 0.0125 mM to to about 1 mM, a more preferred response usually occurs at 0.2 mM to 0.4 mM, especially in cases when the response is low. When the mitogen response is high much less of this compound is required to augment the immune response.

In contrast to its strong and consistent enhancing effects on T cell mitogen induced proliferation, 6-amino-(2-deoxy-α-D-erythro-pentofuranosyl)-imidazo[4,5,-C]pyridin-4-one does not display an augmenting influence on B cell mitogenesis. Thus unlike 8-substituted guanosine analogs, this compound showed neither an effect on *Staphylococcus aureus* cowan induced B cell proliferation nor an increase of B cell activation by Pokeweed mitogen. This, in direct contrast to guanosine analogs, this suggests that 6-amino-(2-deoxy-α-D-erythro-pentofuranosyl)-imidazo[4,5,-C]pyridin-4-one potentiates mainly T cell responses.

The development of alloantigen-specific cytotoxic T lymphocytes or viral or chemically altered autoantigen specific cytotoxic T lymphocytes requires helper T cells or their biologically active molecules such as interleukin-2. The failure to induce these functionally active effectors could be the result of quantitative/qualitative abnormalities in helper T cells or their products. Alloantigen induced proliferation of T cells resulting in the development of cytotoxic T lymphocytes and mixed lymphocyte response is considered to be a measure of helper T cell function.

When added during allogeneic mixed lymphocyte response, the compound 6-amino-(2-deoxy-α-D-erythro-pentofuranosyl)-imidazo-[ 4,5,-C]pyridin-4-one enhances the proliferation of alloreactive T cells in a dose and antigen dependent manner as is shown below.

It has also been found that the compound 6-amino-(2-deoxy-α-D-erythro-pentofuranosyl)-imidazo[4,5,-C]pyridin-4-one can override immunosuppression such as cyclosporin induced immunosuppression. It is effective in overcoming cyclosporin induced suppression in a wide range of concentrations. This result demonstrates that 6-amino-(2-deoxy-α-D-erythro-pentofuranosyl)-imidazo[4,5,-C]pyridin-4-one is able to restore T cell immune response to T cell mitogens in a dose dependent manner. This reconstitution of immune response is essentially complete when the suppression is low, i.e. induced by lower concentration of cyclosporin, whereas, it has a partial (over 50%) reversal effect when the magnitude of the cyclosporin mediated suppression is higher.

Since the compound 6-amino-(2-deoxy-α-D-erythro-pentofuranosyl)-imidazo-[4,5,-C]pyridin-4-one does not directly activate T cells to proliferate and differentiate, while we do not wish to be bound by theory the potentiation signal provided by it are perhaps due to an indirect effect. This could be mediated through T cells or macrophages and/or their soluble cytokines. It is possible that this compound exerts its immunoenhancing activity, at least in part by causing an increased expression of Ia antigens. Since, like interleukin-2, it can augment allogeneic mixed lymphocyte response that results in the generation of alloreactive cytotoxic T lymphocytes, it is suggested that it may induce immunomodulation through increasing the induction of some cytokine such as interleukin-1/interleukin-2.

As is shown in the examples below, the compound 6-amino-(2-deoxy-α-D-erythro-pentofuranosyl)-imidazo[4,5,-C]pyridin-4-one is a T cell response immunomodulator and can amplify both normal and artificially induced low lymphocyte responses to activators such as T cell mitogens and alloantigens. It expresses a pronounced T cell response enhancing activity. Although it not mitogenic by itself, it is able to exert a strong potentiating influence on T but not B cell mitogen induced lymphoproliferation in both normal and immunosuppressed conditions.

MATERIALS AND GENERAL METHODS

Isolation Of Peripheral Blood Mononuclear Cells

Peripheral blood mononuclear cells were isolated from heparinized peripheral blood of normal healthy donors as described in Sharma, B. and S. Gupta, "Antigen-specific primary cytotoxic T lymphocyte response in acquired immune deficiency syndrome (AIDS) and AIDS related complex", *Clin. Exp. Immunol.*, 62:296, 1985. Briefly, blood was diluted 1:1 with Hanks balanced salt solution (HBSS). Peripheral blood mononuclear cells were separated on a Ficoll-Hypaque gradient. The peripheral blood mononuclear cells recovered from the interface were washed three times with HBSS and resuspended in RPMI-1640 containing 100 U/ml penicillin, 100 μg/ml streptomycin 2mM L-glutamine (GIBCO, Grand Island, N.Y.), and 10% heat-inactivated pooled A serum (Irvine Scientific, Irvine, Calif.), hereafter referred as complete medium (CM).

6-Amino-1-(2-deoxy-α-D-erythro-pentofuranosyl)imidazo-[4,5-C1(one)

6-Amino-(2-deoxy-α-D-erythro-pentofuranosyl)-imidazo-[4,5,-C]pyridin-4-one was synthesized according to procedure of Revankar et al. referenced above. The anomeric configuration of this compound was determined by proton nuclear magnetic resonance and spectral characteristics and by single crystal X-ray analysis.

Mitogenic Activity

The ability of 6-amino-(2-deoxy-α-D-erythro-pentofuranosyl)-imidazo[4,5,-C]pyridin-4-one to activate lymphocytes was determined by culturing the cells with and without this compound. Peripheral blood mononuclear cells (1×10⁵/0.2 ml) were cultures in 96 well microtiter plates (Corning, N.Y.) for 72-96 hrs at 37° C. in 5% $CO_2$ humid atmosphere and then for an additional 16 hr in the presence of 1 μCi/well [³H] thymidine (ICN Pharmaceuticals, Inc., Irvine, Calif.). Cells were harvested on glass fiber filter paper using a cell harvester (Skatron, Lier, Norway). The radioactivity was measured in a scintillation counter after suspending the dried filter in scintillation fluid.

Lymphocyte Response To Plant Mitogens

The ability of the compound 6-amino-(2-deoxy-α-D-erythropentofuranosyl)-imidazo[4,5,-C]pyridin-4-one to modulate lymphocyte response to plant mitogens was determined by the modified procedure of Sharma, B., O. Kohashi, M. R. Mickey, and P. T. Terasaki, "Effect of water soluble adjuvants on in vitro lymphocyte immunization", Cancer Res. 35:666, 1975. Peripheral blood mononuclear cells were cultured for 72-96 hr with phytohemagglutinin (Difco, Detroit, Mich.), Concanavalin A (Calbiochem, Calif.) or Pokeweed mitogen (GIBCO, Grand Island, N.Y.) in the presence and absence of 6-amino-(2-deoxy-α-D-erythro-pentofuranosyl)-imidazo[4,5,-C]pyridin-4-one. The culture were set up in quadruplicate and pulsed with [³H]-thymidine for 16 hr and the [³H] thymidine incorporation was determined.

B Lymphocyte Response To *Staphylococcus Aureus* Cowan (SAC)

Peripheral blood mononuclear cells (1×10⁵/0.2 ml/well) were incubated with different concentrations of *Staphylococcus aureus* cowan (1:100, 1:000 and 1:10,000 dilutions) in the presence and absence of 6-amino-(2-deoxy-α-D-erythro-pentofuranosyl)-imidazo[4,5,-C]pyridin-4-one for 4 days. The cultures were pulsed with [³H]-thymidine and then the incorporation of [³H]thymidine was measured.

T Lymphocyte Response To Alloantigens

Peripheral blood mononuclear cells (1×10⁵/0.2 ml/well) from donor-A were cultured together with different numbers of peripheral blood mononuclear cells (1×10⁵/well, 0.5×10⁵/well, or 0.25×10⁵/well) of peripheral blood mononuclear cells from the other donor for 96 hr as previously described above for the lymphocyte response to plant mitogens. Cultures were pulsed with [³H]-thymidine for additional 16 hrs.

Cyclosporin A Induced Suppression Of Lymphocyte Response To Mitogens

Peripheral blood mononuclear cells were cultured with phytohemagglutinin or Concanavalin A in the presence and absence of Cyclosporin A (10 ng/well or 50 ng/well) for 96 hr. Cultures were pulsed for 16 hr and [³H]-thymidine incorporation was measured.

EXAMPLE I

Mitogenic Activity Of 6-Amino-(2-deoxy-α-D-erythro-pentofuranosyl)-imidazo[4,5,-C]pyridin-4-one To determine whether 6-amino-(2-deoxy-α-D-erythro-pentofuranosyl)-imidazo[4,5,-C]pyridin-4-one directly activates lymphocytes to proliferate, peripheral blood mononuclear cells were cultured with or without this compound as described in the above methods section. The results given in Table I show that in the presence of 0.006 mM to 0.4 mM, 6-amino-(2-deoxy-α-D-erythro-pentofuranosyl)-imidazo[4,5,-C]pyridin-4-one caused no significant increase in the proliferation of peripheral blood mononuclear cells from any of several donors examined. A concentration of 1 mM of this compound also failed to stimulate lymphocytes to proliferate.

TABLE I

Effect of 6-Amino-(2-deoxy-α-D-erythro-pentofuranosyl)imidazo[4,5,-C]pyridin-4-one on ³H-thymidine Incorporation in Human Lymphocytes Culture[a]

| Donor of Lymphocytes | ³H-thymidine Incorporation (CMP)[b] Concentration of Test Compound (mM) | | | | | |
|---|---|---|---|---|---|---|
| | 0 | 0.006 | 0.025 | 0.050 | 0.2 | 0.4 |
| 1 | 383 ± 74 | 212 ± 96 | 494 ± 267 | 306 ± 106 | 246 ± 99 | 320 ± 46 |
| 2 | 144 ± 57 | 262 ± 68 | 273 ± 122 | 257 ± 67 | | |
| 3 | 324 ± 81 | 266 ± 42 | 252 ± 112 | 180 ± 37 | | |
| 4 | 257 ± 29 | 246 ± 61 | 237 ± 55 | 240 ± 35 | | |
| 5 | 301 ± 107 | 238 ± 63 | 121 ± 55 | 841 ± 310 | 277 ± 51 | 165 ± 64 |
| 6 | 582 ± 121 | 486 ± 51 | 508 ± 140 | 650 ± 130 | 620 ± 322 | 395 ± 22 |
| 7 | 1506 ± 255 | 1133 ± 257 | 1667 ± 254 | 772 ± 137 | 657 ± 137 | 702 ± 189 |

[a]Peripheral blood mononuclear cells from different donors were incubated in the presence of 6-amino-(2-deoxy-α-D-erythro-pentofuranosyl)-imidazo[4,5,-C]pyridin-4-one for four days and then ³H-thymidine incorporation was determined in the lymphocytes.
[b]Counts per minute.

EXAMPLE II

Effect Of 6-Amino-(2-deoxy-α-D-erythro-pentofuranosyl)imidazo[4,5,-C]pyridin-4-one On Mitogens Induced Proliferation Lymphocytes from different donors where incubated with various concentration of phytohemagglutinin in absence and presence of 6-amino-(2-deoxy-α-D-erythro-pentofuranoxyl)imidazo[4,5,-C]pyridin-4-one. The results as shown in table II demonstrate that this compound induced a striking potentiation of lymphocyte response to phytohemagglutinin from all the 5 donors examined.

TABLE II

Effect of 6-Amino-(2-deoxy-α-D-erythro-pento-furanosyl)imidazo[4,5,-C]pyridin-4-one on Phytohemagglutinin(PHA) Induced Human Lymphocyte Proliferation[a]

| Donor of Lymphocytes | Concentration of PHA (mg/0.2 ml) | 3H-thymidine Incorporation (CMP)[b] in PHA-Stimulated Cultures Absence of Test Compound | Presence of Test Compound | (Conc.) | % Potentiation |
|---|---|---|---|---|---|
| 2 | 0.25 | 14319 ± 2342 | 56362 ± 8650 | (0.1) | 294 |
|   | 1.0 | 78222 ± 11934 | 110155 ± 5101 | (0.05) | 41 |
|   | 4.0 | 83134 ± 5539 | 127102 ± 3001 | (0.038) | 53 |
| 3 | 0.25 | 2950 ± 586 | 34646 ± 6344 | (0.4) | 1074 |
|   | 1.0 | 19686 ± 2399 | 77757 ± 18381 | (0.2) | 295 |
|   |     |               | 61653 ± 12029 | (0.4) | 213 |
|   | 4.0 | 36238 ± 4410 | 88518 ± 7387 | (0.2) | 144 |
|   |     |               | 97950 ± 6240 | (0.4) | 170 |
| 4 | 0.25 | 2576 ± 580 | 28765 ± 4475 | (0.4) | 1171 |
|   | 1.0 | 31799 ± 1684 | 50131 ± 4674 | (0.05) | 88 |
|   |     |               | 91669 ± 7462 | (0.4) | 244 |
|   | 4.0 | 62628 ± 8726 | 119811 ± 2608 | (0.4) | 91 |
| 5 | 0.5 | 38648 ± 5715 | 66109 ± 2263 | (0.05) | 71 |
|   | 1.0 | 44503 ± 4097 | 79690 ± 3113 | (0.2) | 79 |
|   | 4.0 | 46270 ± 8127 | 93966 ± 6505 | (0.2) | 103 |
| 6 | 0.5 | 7689 ± 1970 | 16156 ± 3600 | (0.05) | 110 |
| 7 | 0.125 | 15657 ± 697 | 25657 ± 2488 | (0.4) | 353 |
|   |       |              | 23582 ± 3903 | (1.0) | 317 |

[a]Peripheral blood mononuclear cells from different donors were cultured together with PHA in the absence and presence of 6-amino-(2-deoxy-α-D-erythro-pentofuranosyl)imidazo-[4,5,-C]pyridin-4-one for 4 days and 5th day 3H-thymidine incorporation was determined as described in the text.
[b]Counts per minute.

As is seen in Table III the activity of 6amino-(2-deoxy-α-D-erythro-pentofuranosyl)-imidazo[4,5,-C]pyridin-4-one equals that of interleukin-2 in augmenting phytohemagglutinin response. Activation with phytohemagglutinin was augmented from 41 to 117%. The concentrations of this compound which displayed immunomodulatory activity ranged from 0.035 to 0.4 mM.

TABLE III

Effect of Recombinant Interleukin-2 (rIL-2) on Incorporation of $^3$H-thymidine in Human Phytohemagglutinin(PHA) Induced Mitogens[a] and Mixed Lymphocyte Culture

| Culture (CPM) | rIL-2 (units) | $^3$H-thymidine Incorporation | % Potentiation |
|---|---|---|---|
| A + PHA (2 μg) | — | 85,718 ± 5255 |  |
| A + PHA (1 μg) | + (2) | 109,587 ± 9210 | 23 |
| A + PHA (1 μg) | + (10) | 124,464 ± 9761 | 45 |
| A + PHA (0.125 μg) | — | 12,854 ± 1545 |  |

TABLE III-continued

Effect of Recombinant Interleukin-2 (rIL-2) on Incorporation of $^3$H-thymidine in Human Phytohemagglutinin(PHA) Induced Mitogens[a] and Mixed Lymphocyte Culture

| Culture (CPM) | rIL-2 (units) | $^3$H-thymidine Incorporation | % Potentiation |
|---|---|---|---|
| A + PHA (0.125 μg) | + (5) | 95,849 ± 9225 | 645 |
| A + PHA (0.125 μg) | + (10) | 87,707 ± 3989 | 582 |
| A + B | — | 13,327 ± 922 |  |
| A + B | + (2) | 19,413 ± 2623 | 46 |
| A + B | + (5) | 22,451 ± 2979 | 68 |
| A + B | + (10) | 26,690 ± 1962 | 100 |

[a]Peripheral blood mononuclear cells from donor A (1 × 10$^5$/0.2 ml) were mixed with donor B (1 × 10$^5$ × 0.2 ml) or phytohemagglutinin and incubated in the presence and absence of rIL-2. At the end of incubation period, $^3$H-thymidine incorporation was determined.

The compound also caused a marked increase in lymphocyte response to Concanavalin A as is seen in Table IV.

TABLE IV

Effect of 6-Amino-(2-deoxy-α-D-erythro-pentofuranosyl)-imidazo[4,5,-C]pyridin-4-one on Concanavalin A (Con A) Induced Human Lymphocyte Proliferation[a]

| Donor of Lymphocytes | Concentration of Con A (mg/0.2 ml) | 3H-thymidine Incorporation (CMP)[b] in Con A-Stimulated Cultures Absence of Test Compound | Presence of Test Compound | (Conc.) | % Potentiation |
|---|---|---|---|---|---|
| 2 | 0.13 | 4444 ± 704 | 18607 ± 2157 | (0.2) | 318 |
|   |      |             | 31068 ± 2678 | (0.4) | 599 |
|   | 0.25 | 14825 ± 4487 | 44958 ± 2248 | (0.2) | 203 |
|   |      |               | 48354 ± 3336 | (0.4) | 226 |
|   | 2.0 | 125304 ± 16248 | 162317 ± 10872 | (0.025) | 29 |
| 3 | 0.13 | 19713 ± 3849 | 29693 ± 4998 | (0.0125) | 50 |
|   |      |               | 39902 ± 2918 | (0.4) | 102 |
|   | 0.25 | 42547 ± 2071 | 57780 ± 9762 | (0.05) | 36 |
|   |      |               | 51010 ± 3861 | (0.4) | 20 |
|   | 2.0 | 109733 ± 3252 | 122692 ± 3643 | (0.05) | 12 |
|   |      |               | 98613 ± 4737 | (0.4) | −11 |
| 4 | 0.13 | 20973 ± 8211 | 44234 ± 5027 | (0.05) | 110 |

TABLE IV-continued

Effect of 6-Amino-(2-deoxy-α-D-erythro-pentofuranosyl)-imidazo[4,5,-C]pyridin-4-one on Concanavalin A (Con A) Induced Human Lymphocyte Proliferation[a]

| Donor of Lymphocytes | Concentration of Con A (mg/0.2 ml) | 3H-thymidine Incorporation (CMP)[b] in Con A-Stimulated Cultures | | (Conc.) | % Potentiation |
|---|---|---|---|---|---|
| | | Absence of Test Compound | Presence of Test Compound | | |
| | 0.25 | 26161 ± 3957 | 39059 ± 5098 | (0.05) | 49 |
| | 0.05 | 28588 ± 6363 | 43957 ± 6053 | (0.025) | 54 |
| 1 | 0.25 | 37219 ± 1658 | 49279 ± 2732 | (0.05) | 32 |
| | 1.0 | 53034 ± 2906 | 71105 ± 4015 | (0.006) | 34 |
| | 4.0 | 69394 ± 7566 | 99322 ± 8655 | (0.038) | 43 |
| 5 | 0.5 | 53456 ± 4099 | 71303 ± 3633 | (0.05) | 33 |
| | 2.0 | 64423 ± 7340 | 75046 ± 1495 | (0.025) | 16 |

[a]Peripheral blood mononuclear cells from different donors were cultured together with Con A in the absence and presence of 6-amino-(2-deoxy-α-D-erythro-pentofuranosyl)-imidazo[4,5,-C]pyridin-4-one for 4 days and on the 5th day [b]H-thymidine incorporation was determined.

In Table IV, the 6-amino-(2-deoxy-α-D-erythropentofuranosyl)-imidazo[4,5,-C]pyridin-4-one induced increase ranged from 12 to 599% with a mean increase of 109%. It had a slight suppressive effect in only one case. There was an observed variation in the magnitude of the compound mediated increase in responses of different donors. It is shown to be more effective in cases when the response is low.

Figure 1:
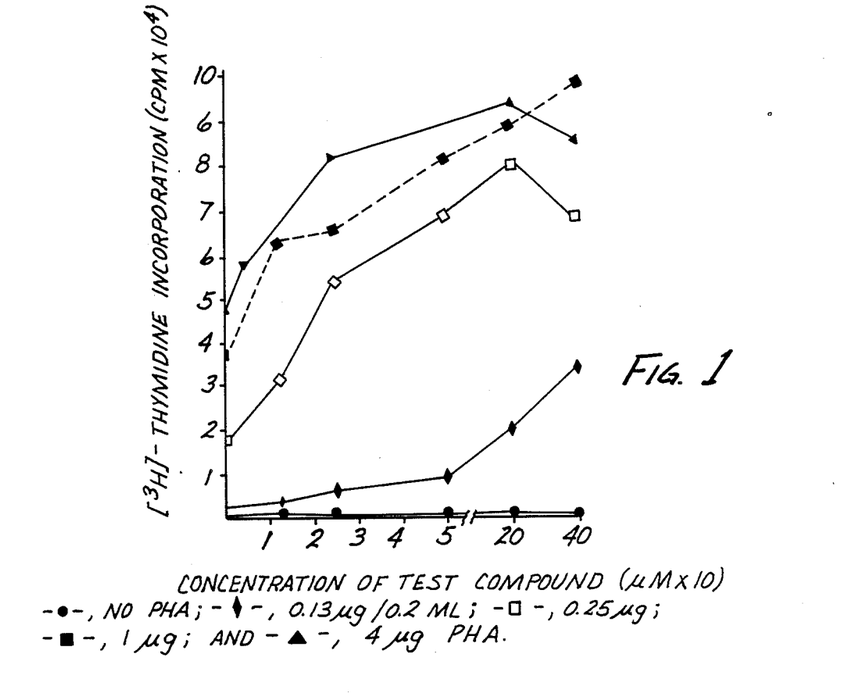
FIG. 1 is a graph of induced increase in lymphocyte proliferation in response phytohemagglutinin and the active compound of the invention.

As shown in FIG. 1, 6-amino-(2-deoxy-α-D-erythropentofuranosyl)-imidazo[4,5,-C]pyridin-4-one induced increase in lymphocyte proliferative response to phytohemagglutinin (PHA). Peripheral blood mononuclear cells were cultured with different concentrations (0, 0.13 μg/0.2 ml, 0.25 μg and 2 μg) of phytohemagglutinin in the presence and absence of 6-amino-(2-deoxy-α-D-erythro-pentofuranosyl)-imidazo[4,5,-C]pyridin-4-one. Lymphocyte proliferation was determined by $^3$H-thymidine incorporation.

Figure 2:
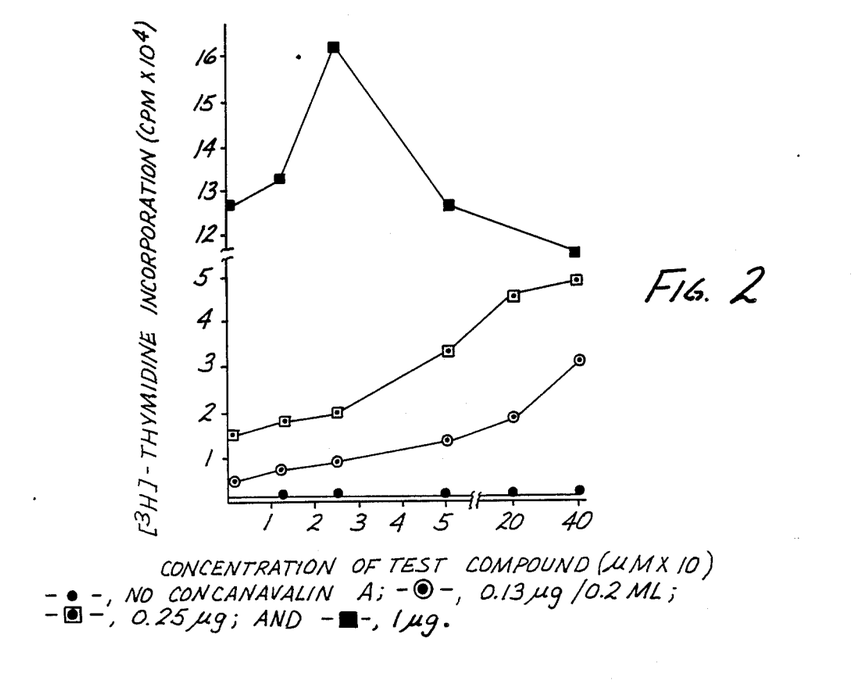
FIG. 2 is a graph of induced increase in lymphocyte proliferation in response to Concanavalin A and the active compound of the invention.

As shown in FIG. 2, 6-amino-(2-deoxy-α-D-erythropentofuranosyl)-imidazo[[4,5,-C]pyridin-4-one induced increase in lymphocyte proliferative response to Concanavalin A (Con A). Peripheral blood mononuclear cells were cultured with different concentrations of Concanavalin A in the presence and absence of 6-amino-(2-deoxy-α-D-erythro-pentofuranosyl)-imidazo[4,5,-C]pyridin-4-one. Lymphocyte proliferation was determined by $^3$H-thymidine incorporation.

In contrast, this compound did not have any significant immunopotentiating effect on Pokeweed mitogen induced proliferation of lymphocytes (a maximum increase of 18%) as is seen in Table V. In fact, it exerted generally a suppressive effect, especially at relatively higher concentrations.

TABLE V

Effect of 6-Amino-(2-deoxy-α-D-erythro-pentofuranosyl)-imidazo[4,5,-C]pyridin-4-one on Pokeweed (PWM) Induced Lymphocyte Proliferation[a]

| Donor of Lymphocytes | $^3$H-Thymidine Incorporation | | (mM) | % Increase (+) or Decrease (−) |
|---|---|---|---|---|
| | Absence of Compound | Presence of Compound | | |
| 1 | 53384 ± 3782 | 62772 ± 2781 | (0.006) | 18 (+) |
| | | 56449 ± 2090 | (0.025) | 8 (+) |
| | | 45844 ± 1152 | (0.05) | 14 (−) |
| | 58731 ± 3351 | 61100 ± 4701 | (0.006) | 4 (+) |
| | | 57852 ± 3166 | (0.025) | 1 (−) |
| | | 54840 ± 942 | (0.05) | 7 (−) |
| 2 | 83825 ± 6006 | 70197 ± 5940 | (0.125) | 16 (−) |
| | | 67565 ± 5857 | (0.025) | 19 (−) |
| | | 67429 ± 3657 | (0.05) | 19 (−) |
| 3 | 42152 ± 4012 | 40425 ± 1158 | (0.006) | 4 (−) |
| | | 32818 ± 4806 | (0.025) | 22 (−) |
| | | 30453 ± 2974 | (0.2) | 27 (−) |
| 4 | 37301 ± 886 | 39090 ± 4853 | (0.006) | 4 (+) |
| | | 33122 ± 4539 | (0.025) | 11 (−) |
| | | 30500 ± 2132 | (0.05) | 18 (−) |

[a]Peripheral blood mononuclear cells from different donors were cultured with pokeweed mitogen in the absence and presence of 6-amino-(2-deoxy-α-D-erythro-pentofuranosyl)-imidazo[4,5,-C]pyridin-4-one for 4 days and then $^3$H-thymidine incorporation was determined.

EXAMPLE III

Effect Of 6-Amino-(2-deoxy-α-D-erythro-pentofuranosyl)imidazo[4,5,-C]pyridin-4-one On *Staphylococcus Aureus* Cowan Induced B Cell Proliferative Response To further evaluate the effect on B cell response, human peripheral blood mononuclear cells were cultured with *Staphylococcus aureus* cowan in the presence and absence of 6-amino-(2-deoxy-α-D-erythro-pentofuranosyl)-imidazo[4,5,-C]pyridin-4-one. The results in shown Table VI show that this compound has no augmenting effect on the *Staphylococcus aureus* cowan induced B cell proliferation. Like the effect on Pokeweed mitogen, it induced slight suppression of B cell proliferation in some cases.

TABLE VI

Effect of 6-Amino-(2-deoxy-α-D-erythro-pentofuranosyl)-
imidazo[4,5,-C]pyridin-4-one
on *Staphylococcus Aureus* Cowan (SAC)
Induced B Cell Proliferation[a]

| Concentration of SAC (Dilution) | 3H-Thymidine Incorporation | | |
|---|---|---|---|
| | Absence of Compound | Presence of Compound | (mM) |
| 1:100 | 31467 ± 2183 | 31582 ± 5535 | (0.0125) |
| | | 30876 ± 1757 | (0.025) |
| | | 31036 ± 2225 | (0.05) |
| | | 31549 ± 1496 | (0.6) |
| 1:1000 | 21478 ± 1546 | 18079 ± 829 | (0.0125) |
| | | 18897 ± 1334 | (0.025) |
| | | 17240 ± 1634 | (0.05) |
| | | 16618 ± 2378 | (0.2) |

[a]Peripheral blood mononuclear cells were cultured with *Staphylococcus Aureaus* Cowan in the presence and absence of 6-amino-(2-deoxy-α-D-erythro-pentofuranosyl)-imidazo[4,5,-C]pyridin-4-one for 4 days and then 3H-thymidine incorporation was determined as described in the text.

EXAMPLE IV

Effect Of
6-Amino-(2-deoxy-α-D-erythro-pentofuranosyl-
)imidazo[4,5,-C]pyridin-4-one On Mixed Lymphocyte
Response (MLS)

This experiment shows 6-amino-(2-deoxy-α-D-erythro-pentofuranosyl)-imidazo[4,5,-C]pyridin-4-one modulates the mixed lymphocyte response (MLR). The results shown in Table VII demonstrate that addition of this compound in 2-way mixed lymphocyte culture markedly increased the mixed lymphocyte response in a dose dependent manner in most of the cases. The maximal increase of 91% is seen in those experiments where allogeneic peripheral blood mononuclear cells. When added during mixed lymphocyte response, recombinant interleukin-2 also caused a similar increase in mixed lymphocyte response (see Table III).

Figure 3:
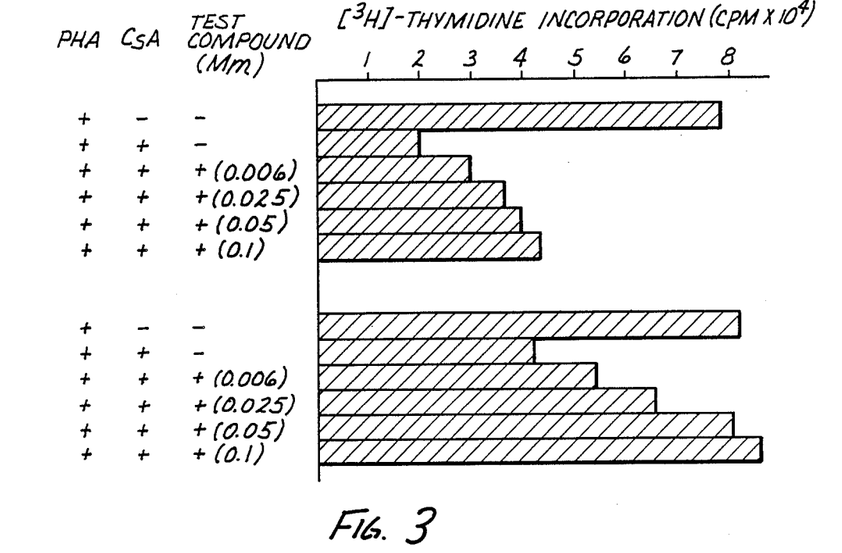
FIG. 3 is a graph showing restoration of Cyclosporin A induced suppression of lymphocyte proliferation in response to phytohemagglutinin and the active compound of the invention.

The results of FIG. 3 demonstrate that Cyclosporin A suppressed the phytohemagglutinin induced T cell proliferation by 75%. In FIG. 3, 6-amino-(2-deoxy-α-D-erythropentofuranosyl)-imidazo[4,5,-C]pyridin-4-one mediated restoration of Cyclosporin A (CsA) induced suppression of lymphocyte proliferative response to phytohemagglutinin (PHA). Peripheral blood mononuclear cells were cultured with phytohemagglutinin in the presence of CsA (10 and 50 ng/0.2 ml) and 6-amino-(2-deoxy-α-D-erythro-pentofuranosyl)-imidazo[4,5,-C]pyridin-4-one. Lymphocytes proliferation was determined by 3H-thymidine incorporation. The addition of 6-amino-(2-deoxy-α-D-erythro-pentofuranosyl)-imidazo[4,5,-C]pyridin-4-one increased the T cell proliferative response in a dose dependent manner from 20,000 CPM (counts per minute) to 43,000 CPM.

In further tests, when Cyclosporin A induced suppression was about half of the total response, 6-amino-(2-deoxy-α-D-erythro-pentofuranosyl)imidazo[4,5,-C]pyridin-4-one completely restored the lymphocyte proliferation.

Figure 4:
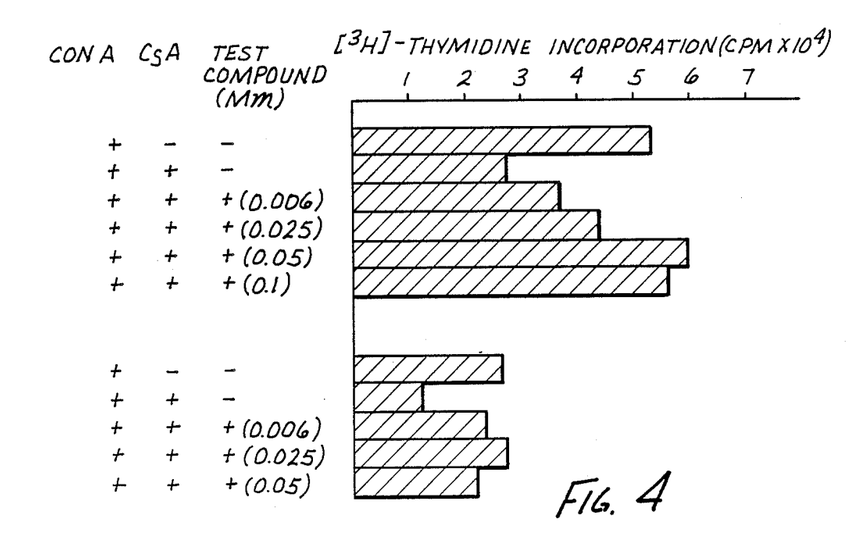
FIG. 4 is a graph showing restoration of Cyclosporin A induced suppression of lymphocyte proliferation in response to Concanavalin A and the active compound of the invention.

Cyclosporin A also suppressed Concaravalin A induced proliferation by about 50% as is seen in FIG. 4. In FIG. 4, 6-amino-(2-deoxy-α-D-erythro-pentofuranosyl)-imidazo[4,5,-C]pyridin-4-one mediated restoration of Cyclosporin A (CsA) induced suppression of lymphocyte proliferative response to Concanavalin A (Con A). Peripheral blood mononuclear cells were cultured with Concanavalin A in the presence of CsA (10 and 50 ng/0.2 ml) and 6-amino-(2-deoxy-α-D-erythro-pentofuranosyl)-imidazo[4,5,-C]pyridin-4-one. Lymphocytes proliferation was determined by 3H-thymidine incorporation. As shown in this figure, test compound also completely reversed this Cyclosporin A mediated suppression.

Cytotoxic T lymphocytes are important in the protection against both tumors and non-self organisms. A further test shows an increase in the induction of cytotoxic T lymphocyte activity by 6-amino-(2-deoxy-α-D-erythro-pentofuranosyl)imidazo[4,5,-C]pyridin-4-one.

TABLE VII

Effect of 6-Amino-(2-deoxy-α-D-erythro-pentofuranosyl)-
imidazo[4,5,-C]pyridin-4-one
on Incorporation of 3H-thymidine in
Human Mixed Lymphocyte Culture[a]

| | 3H-thymidine Incorporation (CPM ± SD)[b] in MLC With Test Compound Concentration of Test Compound (mM) | | | | | |
|---|---|---|---|---|---|---|
| Experiment | 0 | 0.05 | 0.0125 | 0.2 | 0.025 | 0.4 |
| A + B (0.5 × 10^5) | 12276 ± 2252 | 21399 ± 1759 | 14814 ± 929 | 22448 ± 1609 | 18978 ± 1048 | 21593 ± 3007 |
| A + B (1 × 10^5) | 17495 ± 1443 | 33532 ± 1732 | 26858 ± 2392 | 30790 ± 1912 | 21794 ± 7136 | 30261 ± 1835 |
| A + B (2 × 10^5) | 16102 ± 3262 | 25299 ± 4479 | 18608 ± 2511 | 29209 ± 2804 | 23548 ± 4439 | 27940 ± 3679 |
| B + A (0.5 × 10^5) | 13880 ± 1510 | 20799 ± 1068 | 17045 ± 982 | 19346 ± 20799 | 19538 ± 3053 | 13779 ± 3043 |
| B + A (2 × 10^5) | 18925 ± 2577 | 24362 ± 2936 | 18538 ± 1601 | 27737 ± 2105 | 22129 ± 3893 | 28986 ± 1448 |

[a]Peripheral blood lymphocytes from two different normal donors were incubated in the presence and absence of various concentrations of 6-amino-(2-deoxy-α-D-erythro-pentofuranosyl)-imidazo[4,5,-C]pyridin-4-one for four days and 3H-thymidine incorporation was determined on the 5th day.
[b]Counts per minute.

EXAMPLE V

6-Amino-(2-deoxy-α-D-erythro-pentofuranosyl-
)imidazo[4,5,-C]pyridin-4-one Mediate Restoration Of
Cyclosporin A Induced Suppression Of T
Lymphocytes Proliferation This example shows 6-amino-(2-deoxy-α-D-erythro-pentofuranosyl)-imidazo[4,5,-C]pyridin-4-one restores a Cyclosporin A induced suppression of T cell proliferative response. Peripheral blood mononuclear cells from normal donors were incubated with T cell mitogens in the presence and absence of this compound and then [3H-thymidine incorporation was measured.

EXAMPLE VI

6-Amino-(2-deoxy-α-D-erythro-pentofuranosyl)-
imidazo-[4,5,-C]pyridin-4-one Potentiation of
Generation of Antigen-Specific Primary Cytotoxic T
Lymphocytes Peripheral blood mononuclear cells from healthy donor A and C were cultured together with irradiated (3000 R) peripheral blood mononuclear cells from donor B and irradiated cells (SX) from B cells of the SB cell line, respectively, for five days. At the end of the incubation period, the cells were washed and resuspended in medium and then their cytotoxic activity was determined against the specific lymphoblast target cell B or S according to the procedure of Sharma and Gupta noted above.

The results shown in table VII demonstrate that 6-amino-(2-deoxy-α-D-erythro-pentofuranosyl)-imidazo[4,5,-C]pyridin-4-one is capable of potentiating the generation of antigen-specific cytotoxic T lymphocyte activity against alloantigens. The cytotoxic T lymphocyte activity against specific fresh phytohemagglutinin induced lymphoblasts as well as against cultured lymphoblasts from the SB cell (leukemic) line was increased by this compound.

TABLE VIII

Effect of 6-Amino-(2-deoxy-α-D-erythro-pentofuranosyl)-imidazo[4,5,-C]pyridin-4-one
on Potentiation of Induction of Antigen-Specific
Primary Cytotoxic T Lymphocytes[a]

| Exp. # | Mixed Culture Concentration[b] | Target Cells | % Specific Cytotoxicity |
|---|---|---|---|
| 1 | A + Bx | B[c] | 7 |
|  | A + Bx + Test Compound (0.05) | B | 9 |
|  | A + Bx + Test Compound (0.1) | B | 22 |
|  | A + Bx + Test Compound (0.2) | B | 26 |
| 2 | C + Sx | S | 26 |
|  | C + Sx + Test Compound (0.006) | S | 42 |
|  | C + Sx + Test Compound (0.025) | S | 36 |
|  | C + Sx + Test Compound (0.1) | S | 53 |

[a]Peripheral blood mononuclear cells from healthy donor A were cultured together with irradiated stimulatory peripheral blood mononuclear cells from donor B for 5 days. Peripheral blood mononuclear cells from donor C were cultured with irradiated cells (S) from B cells of the SB cell line. The cytotoxicity of cultured cells was then tested against the assay specific B or S target cells in a $^{51}$Cr release assay.
[b]Concentration.
[c]Donor B.

The compound when given concurrently with an antigen during immunization as, for instance concurrently with an influenza vaccine, will augment the response to the immunization antigen to potentiate the immune response.

T cell mitogen and antigen response have been shown to be deficient or depressed with aging. Since 6-amino-(2-deoxy-α -D-erythro-pentofuranosyl)imidazo[4,5,-C]pyridin-4-one increase both mitogen and antigen response, its use in treating these conditions in aging is implicated.

The compound of the invention can be given to a human or animal host in need thereof in appropriate formulations wherein the compound comprise the active ingredient of the formulations. Thus the compound of the invention can be made up into injectables suitable for intravenous or other type injection into the host animal. Further it can be given in an appropriate oral formulation as for instance as an oral syrup preparation, an oral capsule or oral tablet. An additional route of administration might be as a suppository.

For an injectable the compound would be dissolved in a suitable solution as for instance in a sodium bicarbonate or other buffer. Such a solution would be filtered and added to appropriate ampoules or vials and sealed and sterilized.

As a syrup, the compound in buffered solution would be mixed with an appropriate syrup with mild stirring. For capsules the dry compound would be blended with appropriate fillers, binders or the like as for instance Lactose USP powder or Sterotex powder. For the preparation of tablets the compound of the invention would be mixed with suitable binders and fillers as for instance corn starch NF, Microcrystalline Cellulose, Sterotex powder and water and dried to a low water content. This would be followed by screening, milling, further screening and pressing into the appropriate tablets.

For suppositories, the compound would be dissolved into appropriate melts of Polyethylene Glycol as for instance Polyethylene Glycol 1540 and 8000 at 60° and formed into the suppositories by molding at 25°.

In addition to the above formulations, the compound of the invention could also be administered utilizing other delivery technique such as incorporating the compound of the invention with liposomes and the like.

Additionally, prodrug forms of the compound of the invention could be utilized to facilitate dispensing, uptake, absorption, metabolic control and the like. One such prodrug would be the tri-acetate ester. Further prodrugs might allow for enzymatic conversion in vivo of analogs of the compound of the invention into the compound of the invention, e.g. the 5'-phosphate analog might be enzymatic convered.

We claim:
1. A immunoenhancing composition comprising an antigen and a diluent amount of a physiologically tolerable carrier admixed with an immunoenhancing effective amount of the compound 6-amino-(2-deoxy-α-D-erythro-pentofuranosyl)-imidazo[4,5,-C]pyridin-4-one or pharmaceutically acceptable salts thereof.

2. A immunoadjuvant composition for human or animal cells comprising a T cell mitogenic agent and a diluent amount of a physiologically tolerable carrier admixed with an immunoadjuvant effective amount of the compound 6-amino-(2-deoxy-α-D-erythro-pentofuranosyl)-imidazo[4,5,-C]pyridin-4-one or pharmaceutically acceptable salts thereof.

3. A composition for proliferating alloreactive T cells comprising an alloantigen and a diluent amount of a physiologically tolerable carrier admixed with a proliferative effective amount of the compound 6-amino-(2-deoxy-α-D-erythropentofuranosyl)-imidazo[4,5,-C]pyridin-4-one or pharmaceutically acceptable salts thereof.

4. A composition for potentiating cytotoxic T lymphocytes in human or animal cells comprising a specific antigen and a diluent amount of a physiologically tolerable carrier admixed with a potentiator effective amount of the compound 6-amino-(2-deoxy-α-D-erythro-pentofuranosyl)-imidazo-[4,5,-C]pyridin-4-one or pharmaceutically acceptable salts thereof.

5. A composition for control of depressed cytotoxic T cell function comprising an immunosuppressive agent and a diluent amount of a physiologically tolerable carrier admixed with an restorative effective amount of the compound 6-amino(2-deoxy-α-D-erythro-pentofuranosyl)-imidazo[4,5,-C]pyridin-4-one or pharmaceutically acceptable salts thereof.

6. A method of enhancing an immune response comprising contacting a cellular population which includes T lymphocytes with an immunoenhancing composition including as its active ingredient an amount of the compound 6-amino-(2-deoxy-α-D-erythro-pentofuranosyl)-imidazo[4,5,-C]pyridin-4-one effective to enhance an immune response.

7. A method of enhancing an immune response comprising contacting T lymphocytes with a T cell mitogen and a composition including as an active immunoadjuvant ingredient an amount of the compound 6-amino-(2- deoxy-α-D-erythro-pento-furanosyl)-imidazo[4,5,-C]pyridin-4-one effective to augment the mitogenic immune response.

8. A method of enhancing an alloreactive T cell response comprising contacting T lymphocytes with an alloantigen and a composition including as an active proliferative ingredient an amount of the compound 6-amino-(2-deoxy-α-D-erythro-pentofuranosyl)-imidazo[4,5,-C]pyridin-4-one effective to induced an allogeneic proliferative response.

9. A method of potentiating antigen specific cytotoxic T lymphocytes comprising contacting T lymphocytes in the presence of a specific antigen with an composition including as an active antigen specific T lymphocyte potentiating ingredient an amount of the compound 6-amino-(2-deoxy-α-D-erythro-pentofuranosyl)-imidazo[4,5,-C]pyridin-4-one effective to potentiate the generation of antigen specific cytotoxic T lymphocytes.

10. A method for the restoration of depressed cytotoxic T cell function comprising contacting T lymphocytes with an immunoenhancing composition including as its active ingredient an amount of the compound 6-amino-(2-deoxy-α-D-erythro-pentofuranosyl)-imidazo[4,5,-C]pyridin-4-one effective to stimulate a restorative response of T cell function.

* * * * *

UNITED STATES PATENT AND TRADEMARK OFFICE
CERTIFICATE OF CORRECTION

PATENT NO. : 4,950,647

DATED : AUGUST 21, 1990

INVENTOR(S) : ROLAND K. ROBINS, ET AL.

It is certified that error appears in the above-identified patent and that said Letters Patent is hereby corrected as shown below: ON THE TITLE PAGE:

In the first line of the text of the Abstract "6-Amino-1-(2-deoxy-αD-erythro-pentofuranosyl" should read -- 6-Amino-1-(2-deoxy-α-D-erythro-pentofuranosyl --.

Column 1, line 57, "P.E. D.A." should read -- P.E., D.A. --.

Column 5, line 40, "analogs, this suggests" should read --analogs, suggests--.

Column 5, line 56, "imidazo-[   4,5,-C]" should be -- imidazo-[4,5,-C] --.

Column 6, line 54, "[4,5-Cl(one)" should read -- [4,5-C]pyridin-4-one --.

Column 7, line 24, "culture" should read --cultures--.

Column 9, line 31, "6amino" should be -- 6-amino --.

Column 11, line 63, "imidazo[[4,5,-C]pyridin" should be --imidazo[4,5,-C]pyridin --.

UNITED STATES PATENT AND TRADEMARK OFFICE
CERTIFICATE OF CORRECTION

PATENT NO. : 4,950,647

DATED : AUGUST 21, 1990

INVENTOR(S) : ROLAND K. ROBINS, ET AL.

It is certified that error appears in the above-identified patent and that said Letters Patent is hereby corrected as shown below:

Column 13, lines 33 and 34, "where allogeneic" should be -- where $1 \times 10^5$ responder cells were stimulated with the same number of allogeneic --.

Column 13, line 68, "[$^3$H-" should read -- $^3$H- --.

Column 15, line 43, "2-deoxy-$\alpha$ -D-" should be -- 2-deoxy-$\alpha$-D- --.

Signed and Sealed this

Fifteenth Day of December, 1992

Attest:

DOUGLAS B. COMER

*Attesting Officer*    *Acting Commissioner of Patents and Trademarks*